United States Patent [19]
Behme et al.

[11] Patent Number: 4,594,929
[45] Date of Patent: Jun. 17, 1986

[54] MICROTOME HAVING SPECIMEN RETRACTION MEANS

[75] Inventors: Werner Behme, Walldorf; Manfred Berleth, Eppelheim, both of Fed. Rep. of Germany

[73] Assignee: Parke, Davis & Company, Morris Plains, N.J.

[21] Appl. No.: 696,361

[22] Filed: Jan. 30, 1985

[30] Foreign Application Priority Data

Feb. 7, 1984 [DE] Fed. Rep. of Germany ....... 3404098

[51] Int. Cl.$^4$ ............................................. G01N 1/06
[52] U.S. Cl. ........................................ 83/715; 83/412; 83/915.5
[58] Field of Search ................. 83/409, 412, 414, 703, 83/713–716, 915.5

[56] References Cited

U.S. PATENT DOCUMENTS

| | | | |
|---|---|---|---|
| 3,293,972 | 12/1966 | Burkhardt et al. | 83/414 |
| 3,926,085 | 12/1975 | Shatzel | 83/915.5 |

Primary Examiner—James M. Meister
Attorney, Agent, or Firm—Alan H. Spencer

[57] ABSTRACT

A microtome provided with a drive wheel mounted in a stand, to be actuated manually and/or by means of a drive motor for generating a vertical relative movement between a specimen holder and a cutting knife, has a specimen holder, having a specimen clamping mechanism, arranged so as to be horizontally displaceable in a vertically drivable guide mechanism by means of a cutting-thickness adjustment mechanismn. The adjustment mechanism can horizontally displace the specimen holder through a cutting thickness adjustment distance towards the cutting knife. A specimen retraction mechanism serves to displace horizontally the specimen holder from an unretracted position to a retracted position, the retracted position being further from the cutting knife than the unretracted position. The distance between the retracted position and the unretracted position is greater than the maximum cutting thickness adjustment distance.

10 Claims, 4 Drawing Figures

MICROTOME HAVING SPECIMEN RETRACTION MEANS

BACKGROUND OF THE INVENTION

The invention relates to a microtome having specimen retraction means.

Retraction of a specimen holder having a specimen clamping mechanism in which a specimen is clamped, relative to a fixed cutting knife after a cut has been made is generally known in microtomy. As a result of this retraction, the cutting knife is protected from damage, so that the useful life of the cutting knife is increased. Also, as a result of this retraction the cut surface of the specimen is protected against scratches and damage during the return movement, so that accurate working is possible.

Retraction of the specimen is necessary particularly in the thin-section cutting of hard specimens or in the thin-section cutting of specimens embedded in plastic, in order to achieve a perfect quality of cut and a long useful life of the cutting knife.

It is also known to provide a cutting thickness adjuster which can adjust the position of the specimen holder, usually towards the cutting knife, by a cutting thickness adjustment distance.

In known microtomes, the size of the retraction of the specimen holder is of an order of magnitude which can be less than the maximum possible cutting-thickness adjustment distance, so that it is not possible to prevent incorrect operation when the distance retraction of the specimen is less than the cutting-thickness adjustment distance. This fact presents problems, particularly when the adjustment of the cutting-thickness takes place not when the specimen holder is in position before a cut, but before this, when it is in its position immediately after a cut and before the return of the specimen holder to the cutting position. Moreover, in known microtomes, the specimen retraction mechanism, is an expensive combination of gear wheel and/or spring mechanisms, which can adversely affect the ease of movement of a microtome of this type. Furthermore, in known microtomes, the drive wheel which is provided for generating vertical movement of the specimen holder in order to execute a cut, can rotate in one direction only.

SUMMARY OF THE INVENTION

It is an object of the present invention to improve a microtome of the foregoing type, in such a way that incorrect operation is prevented and that the ease of movement of the microtome is not adversely affected by the automatic specimen retraction mechanism.

According to the present invention there is provided a microtome comprising a specimen holder having specimen clamping means for clamping a specimen to be cut, a cutting knife for cutting the specimen, guide means, a stand, a drive wheel mounted to the stand for generating a vertical movement in the guide means and the specimen holder, cutting thickness adjustment means adapted to displace horizontally the specimen holder relative to the guide means in order to adjust the position of the specimen holder by a cutting thickness adjustment distance, and specimen retraction means adapted to displace horizontally the specimen holder relative to the guide means from an unretracted position to a retracted position, wherein the retracted position is further from the cutting knife than the unretracted position, and the distance between the retracted position and the unretracted position is greater than the maximum cutting thickness adjustment distance.

The guide means and specimen holder may be vertically movable between an uppermost position located above the cutting knife and a lowermost position located below the cutting knife. Typically the specimen would be cut during the downward movement of the specimen holder and guide mechanism.

Because the distance between the retracted and unretracted positions of the specimen holder is greater than the maximum possible cutting-thickness adjustment distance made by means of the cutting-thickness adjustment means, it is possible to carry out the cutting-thickness adjustment immediately following a cut, since as a result of the greater play the cut specimen is at all times spaced from the cutting knife edge during the upward movement. This ensures that damage both to the cutting knife and to the cut surface of the specimen is prevented.

Preferably biasing means is provided for biasing the specimen holder towards the unretracted position.

Desirably the specimen retraction means comprises at least one spring element and a vertically orientated guide rail, the or each spring element being disposed between the stand and the guide rail, said guide rail being horizontally displaceable by a distance at least as great as the distance between the retracted and unretracted positions.

Preferably a lever is pivotally mounted on the guide means and pivotally engages the specimen holder, and said lever engages the guide rail.

This combination of the vertically arranged guide rail and the lever resting against the rail makes possible the achievement a good transmission which increases the ease of operation of the microtome. Moreover, the specimen holder and the drive wheel can always assume the same vertical position relative to one another along the entire guide rail. Furthermore, the guide rail moves only at the start of the upward or downward movement of the specimen holder. This means that the specimen holder is retained reliably both either in the cutting position (i.e. the unretracted position) or in the retracted position, when the guide mechanism and specimen holder are moving vertically; this contributes substantially to the ease of operation of the microtome.

The specimen holder may be provided with an extension and a stop device, the stop device being located on a side of a bearing cover opposite the specimen clamping means and being connected to said lever. The stop device may be fastened to the extension.

The cutting thickness adjustment means may comprise a mechanical cutting thickness adjustment mechanism.

In addition an electromechanical rough cutting thickness adjustment mechanism may be provided for adjusting the cutting thickness by larger distances.

The mechanical adjustment mechanism may be in the form of a known micrometer which is disposed on the extension of the specimen holder.

The distance between the retracted and the unretracted positions may for example be about 250 $\mu$m. In this case, the cutting-thickness adjustment may be about 60 $\mu$m at maximum and the rough cutting-thickness adjustment about 150 $\mu$m at maximum, so that a distance of at least 40 $\mu$m always remains between the edge of the cutting knife and the specimen during the retraction of the specimen, thereby preventing damage to the knife edge and to the cut surface of the specimen. Because the pivotably mounted lever interacts with the resiliently mounted guide rail of the specimen retraction means, a microtome which can be actuated very easily by means of a hand wheel is obtained in a particularly advantageous manner.

The biasing means, which may be located between the guide means and the specimen holder, can have a spring constant which is less than the spring constant of the spring element of the specimen retraction means. In this way, depending on the position of the manually operable drive wheel and consequently of the specimen retraction means, either the biasing means located between the guide means and the specimen holder is activated, in which case the spring element of the specimen retraction means is inactive, or the spring element of the specimen retraction means, with its greater spring constant, is activated, so that the specimen holder is displaced horizontally to the retracted position.

Since, in the microtome of the invention, the specimen retraction means does not require any gearwheels, the microtome has the advantage that it moves very easily.

The spring element of the specimen retraction means may comprise two compression springs located between the stand of the microtome and the vertical guide rail, and the biasing means located between the guide means and the specimen holder may have one or more spring washers.

The specimen retraction means can include an eccentric pin positioned parallel to a shaft of the drive wheel and can have a cam wheel which is mounted rotatably on the same shaft and into which the eccentric pin extends, the cam wheel being aligned within a frame incorporating the guide rail. Over the range of angular rotation of the drive wheel in which the specimen holder is in the retracted position, the spring force of the specimen retraction means counteracts the force of the biasing means located between the guide means the specimen holder, so that the spring forces essentially cancel one another. In this way ease of operation of the microtome is ensured, and to drive the specimen retraction means it is sufficient if a relatively thin eccentric pin engages with the cam wheel. Because the vertically displaceable guide rail, which is also horizontally displaceable at least by the distance between the retracted and unretracted positions, is arranged in alignment with the cam wheel, the space required for the specimen retraction means is reduced to a minimum in an advantageous manner.

In an embodiment of the microtome according to the invention, the cam wheel has a smaller radius over one-half of its periphery than over the other half of its periphery, the diametrically opposed transitions between the different radii being continuous. On a base portion of the frame of the specimen retraction means lying parallel to the guide rail, a cam follower can be provided which engages the periphery of the cam wheel. This cam follower engages the cam wheel at least over the half of the periphery having the larger radius, so that during the rotation of the cam wheel the frame of the specimen retraction means, along this half of the periphery, urges the guide rail towards the stand of the microtome and compresses the compression springs located between the guide rail and the stand.

In this way, the compression springs located between the rail and the stand are inactive, and the biasing means located between the guide means and the specimen holder is activated and bias the specimen holder towards the unretracted position, that is towards the cutting knife. During the rotation of the cam wheel over the half of the periphery which has the smaller radius, the cam follower of the specimen retraction means does not necessarily have to rest against the cam wheel, so that the compression springs located between the guide rail and the microtome stand urge the rail, together with the lever engaging the rail, away from the stand. This causes the specimen holder to move to the retracted position. Advantageously, therefore, during one-half of the rotary movement of the cam wheel the biasing means located between the guide means and the specimen holder is activated alone, and during the second half of this rotary movement it is only the difference between the forces of the biasing means and the forces of the spring elements of the specimen clamping means that takes effect.

In a preferred embodiment of the invention, the cam wheel is provided with a concentric slot, in the form of a circular arc, dimensioned so that the eccentric pin extending into the slot can execute a movement through 180° between end stops disposed at opposite ends of the slot. This slot in the cam wheel permits the drive wheel to be rotated manually both in the clockwise and anticlockwise directions.

When the direction of rotation is reversed, the eccentric pin moves the specimen holder past the cutting knife when the crank of the drive wheel is at only a short distance from the cutting knife, so the torque in respect of the crank is low even when high cutting forces are involved, for example, in the case of hard specimens. This ensures ease of operation of the microtome and prevents the drive from tilting. The possibility of reversing the direction of rotation of the drive wheel is also advantageous in conjunction with the comparatively large play (i.e. the distance between the retracted and unretracted positions), because in this way any cutting-thickness adjustment distance that may be desired is possible in both directions of rotation of the drive wheel, without the possibility of damage to the cutting knife or to the cut surface of the specimen.

The guide rail of the specimen retraction means can have a length corresponding at least to the maximum vertical movement of the guide means. The advantage of such a design of the guide rail is that the vertical cutting movement, which can be of the order of 60 mm in one embodiment of the microtome according to the invention, can be fully utilised. This is often impossible in known microtomes, because the cutting forces are activated at points which can become displaced, in contrast to the precisely defined points which, in the microtome according to the invention, are determined by the end stops in the slot of the cam wheel.

The lever which engages the specimen retraction means, and which serves to move the specimen holder from the untretracted position to the retracted position, can include a follower means at one end, which follower means engages the vertical guide rail. This follower means and the cam follower located on the base portion of the specimen retraction means can be designed as rotary bearings, such as ball or roller bearings. By means of bearings of this type, the friction between the this end of the lever and the guide rail, and the friction between the cam wheel and the frame of the specimen retraction means resting against the cam wheel, are limited to a minimum, and assist in achieving the object on which the invention is based, namely to increase the ease of operation of the microtome.

BRIEF DESCRIPTION OF THE DRAWINGS

Further details, features and advantages will appear from the following description of an exemplary embodiment of the invention illustrated in the drawings, in which.

DETAILED DESCRIPTION

Figure 1:
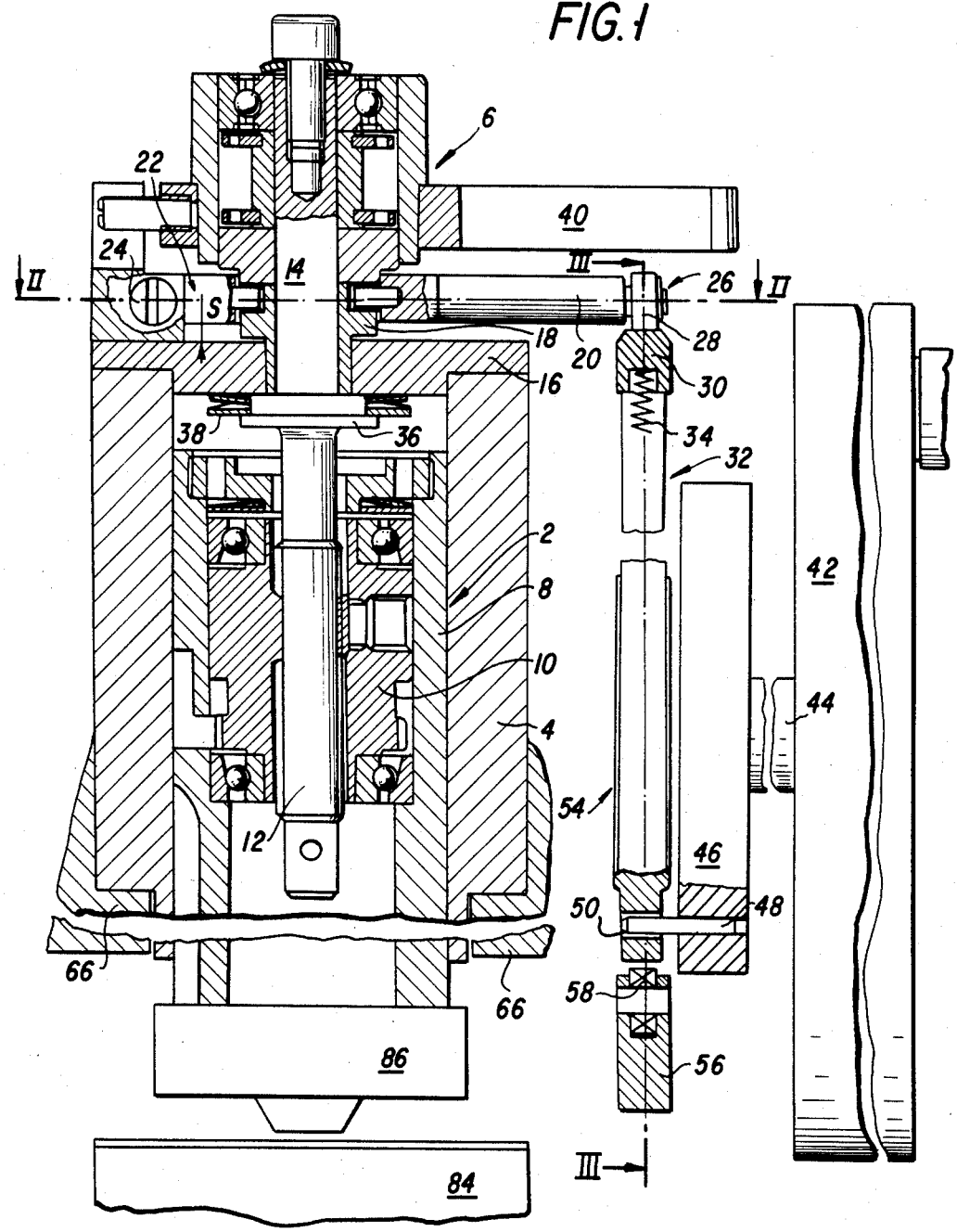
FIG. 1 shows a longitudinal section through a microtome according to the invention, shown partly in section.

In the drawings a microtome 80 includes a specimen holder 2 disposed in guide means in the form of a guide mechanism 4. The guide mechanism 4 and specimen holder 2 are vertically movable relative to the microtome 80. The specimen holder 2 is horizontally displaceable relative to the guide mechanism 4 and a mechanical cutting thickness adjustment mechanism 6 is provided to displace the specimen holder 2 horizontally.

The specimen holder 2 includes a sleeve 8 which is displaceable in the guide mechanism 4, and a micrometer nut 10 is mounted in the sleeve 8 so that it is secured against axial displacement relative thereto. Specimen clamping means in the form of a specimen clamping mechanism 86 is secured to one end of the sleeve 8, and a specimen 90 is clamped by the specimen clamping mechanism 86. The specimen clamping mechanism 86 and the specimen 90 are shown diagrammatically.

A micrometer spindle 12 extends through the micrometer nut 10 and carries at one end an extension 14 which extends through a cover 16. The cover 16 is screwed to the guide mechanism 4 of the specimen holder 2. The spindle 12 has a screw thread upon which the micrometer nut 10 is mounted.

Figure 2:
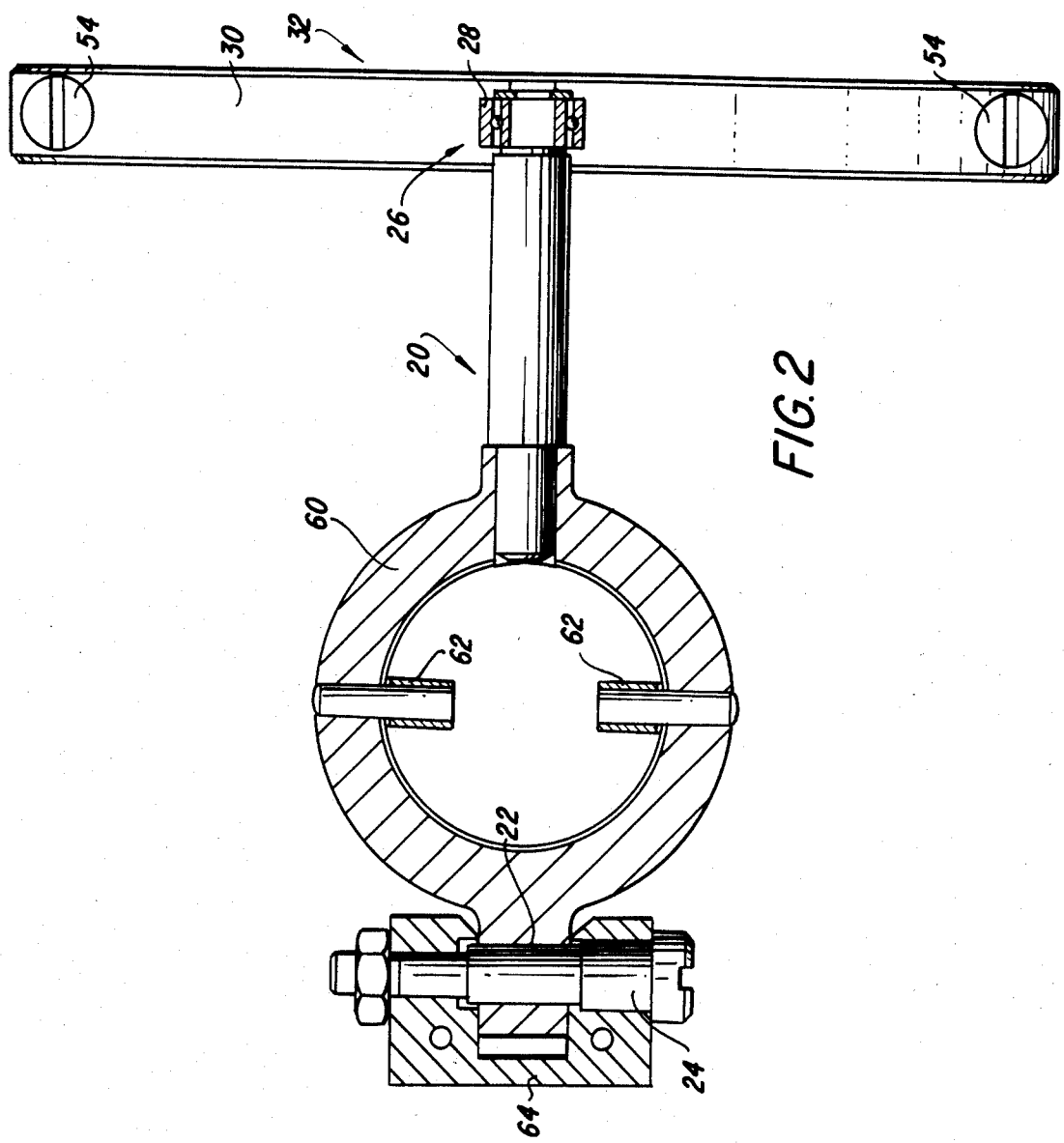
FIG. 2 is a section along lines II—II of FIG. 1.
Figure 3:
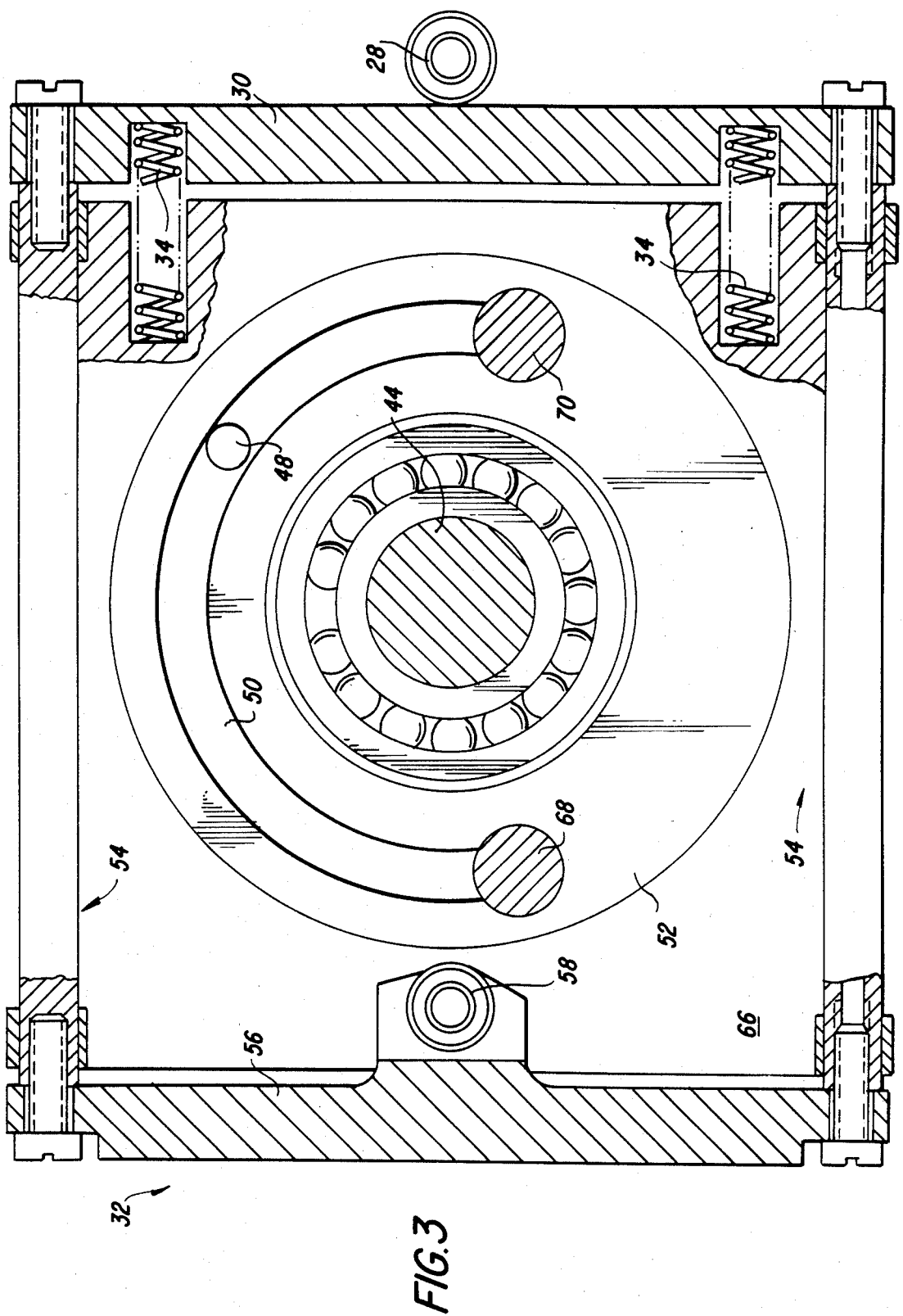
FIG. 3 is a section along lines III—III of FIG. 1.

A stop device 18 is secured to the extension 14 of the micrometer spindle 12. A lever 20 is mounted pivotally between the stop device 18 and the adjustment mechanism 6. The lever 20 is located between the stop device 18 and the adjustment mechanism 6 by means of an annular portion 60 (see FIG. 2). The lever 20 has opposite ends 22 and 26. The end 22 of the lever 20 is pivotally mounted about a screw bolt 24. The screw bolt 24 is secured to an extension 64 of the cover 16. The lever 20 includes follower means 28 in the form of a ball bearing to which the end 26 is secured. The follower means 28 engages a guide rail 30 of specimen retraction means in the form of a specimen retraction mechanism 32. The guide rail 30 is connected to a frame 54 of the specimen retraction mechanism 32.

The micrometer spindle 12 includes a flange 36, and coil springs 38 are disposed between the flange 36 and the inside of the cover 16.

A rotatable drive wheel 42 is provided for moving the guide mechanism 4 vertically up and down in a known manner.

The adjustment mechanism 6 includes a lever 40 which interacts with a cam device (not shown). At each rotation of the drive wheel 42 a lever 40 is rotated through a specific angle of rotation in either the clockwise or anticlockwise direction in a known manner. The extension 14 of the micrometer spindle 12 is rotated through the same angle and this causes the micrometer nut 10, which is secured against rotation, to be displaced axially forwards on the micrometer spindle 12 towards a cutting knife 84, by exactly the amount of a cutting thickness adjustment distance. This causes the sleeve 8 and the specimen clamping mechanism 86 also to move towards the cutting knife 84 by the amount of the cutting thickness adjustment distance.

The drive wheel 42 is connected by a shaft 44 to a disc 46 which carries an eccentric pin 48 extending parallel to the shaft 44. A cam wheel 52 is disposed in the frame 54 and is provided with a slot 50 configured in the form of a circular arc, and arranged concentrically with the shaft 44. The pin 48 extends into the slot 50. An end stop 68 is provided at one end of the slot 50, and an end stop 70 is provided at the other end of the slot 50. The slot 50 is dimensioned so that the eccentric pin 48 can execute a movement through 180° between the end stops 68 and 70 of the slot.

The frame 54 of the specimen retraction mechanism 32 is provided with a base part 56 which extends parallel to the guide rail 30. A cam follower 58, in the form of a ball bearing, is provided on the base part 56 and is urged towards the periphery of the cam wheel 52 by spring elements 34 of the specimen retraction mechanism 32. The spring elements 34 comprise two compression springs located between a microtome stand 66 and the guide rail 30. The spring constant of the coil springs 38 is less than the spring constant of the spring elements 34.

The cam wheel 52 has a smaller radius along one-half of its periphery than along the other half of its periphery, the diametrically opposed transitions between the different radii being continuous.

The guide rail 30 of the specimen retraction mechanism 32 has a length which is at least equal to the vertical movement of the guide mechanism 4.

A motor 82 is provided for driving the drive wheel 42, so that the drive wheel can be rotated either manually and/or by using the motor.

The operation of the microtome according to the invention will now be described.

Figure 4:
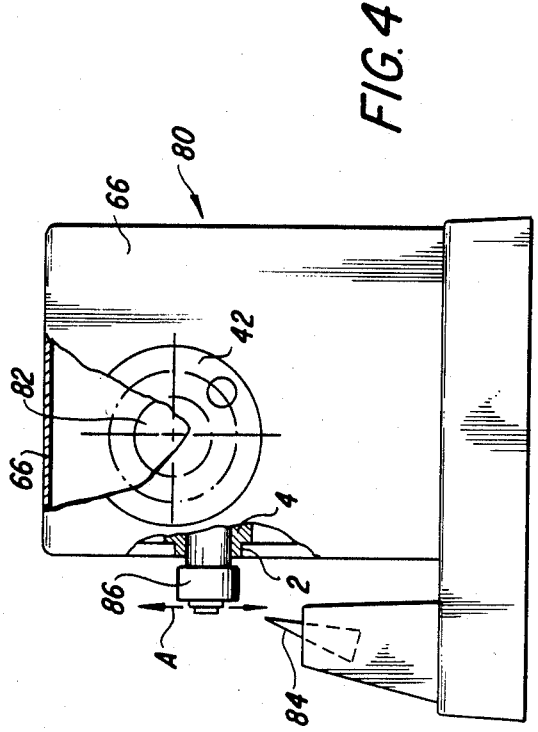
FIG. 4 is an elevation of a microtome according to the invention, with part cut away.

Rotation of the drive wheel 42 causes the guide mechanism 4, together with the specimen holder 2, to move vertically either upwards or downwards (indicated by arrows A in FIG. 4). The guide mechanism 4 is movable between an uppermost position in which the specimen clamping mechanism 86 and specimen 90 are disposed above the cutting knife 84, and a lowermost position in which the specimen clamping mechanism 86 and specimen 90 are disposed below the cutting knife 84.

A single rotation of the drive wheel 42 is sufficient to cause the guide mechanism 4 to move through one cycle of movement, for example, from the lowermost position to the uppermost position, then back to the lowermost position. At the end of one cycle of movement the cam device operating the lever 40 causes the specimen holder 2 to be adjusted in a direction towards the cutting knife 84 by an amount equal to the cutting thickness adjustment distance. This distance can be chosen in advance and may, for example, be of the order of 60 μm. The microtome 80 may typically be arranged so that this adjustment is performed when the guide mechanism 4 is in the lowermost position.

The specimen retraction mechanism 32 serves to retract the specimen holder 2 from an unretracted position by a distance "S" (see FIG. 1) to a retracted position by moving the specimen holder 2 in a direction away from the cutting knife 84 when the guide mechanism 4 reaches the lowermost position. The specimen holder 2 remains in the retracted position during movement from the lowermost to the uppermost position.

The distance "S" indicates the amount of play in the specimen holder between the retracted and unretracted positions.

Rotation of the drive wheel 42 in, for example, a clockwise direction causes the pin 48 to move freely through the slot 50 until it engages the end stop 68. Rotation in an anticlockwise direction causes the pin 48 to move freely through the slot 50 until it engages the end stop 70. Once the pin 48 engages one of the end stops 68 or 70, continued rotation causes the cam wheel 52 also to rotate in the direction of rotation of the drive wheel 42, one revolution of the drive wheel 42 corresponding to one revolution of the cam wheel 52.

During one-half of each rotation of the cam wheel 52 the portion of the cam wheel 52 having the larger diameter is in contact with the cam follower 58. This urges the base 56 of the frame 54 away from the centre of the cam wheel 52, and draws the guide mechanism 30 towards the microtome stand 66 against the spring force of the spring elements 34; this causes compression of the spring elements 34.

In this position the guide mechanism 30 is not urged towards the follower means 28, so the spring force of the coil springs 38 acting between the cover 16 and the flange 36 urges the specimen holder 2 towards the cutting knife 84, i.e. towards the unretracted position.

During the other half of each rotation of the cam wheel 52, the portion of the cam wheel 52 having the smaller diameter is in contact with the cam follower 58. During this half rotation, the spring elements 34 urge the guide rail 30 and the frame 54 away from the microtome stand 66 towards the follower means 28. The force of the guide rail 30 on the follower means 28 urges the follower means 28 together with the lever 20 away from the microtome stand 66, and this exerts the force on the specimen holder 2 which retracts the specimen holder 2 by the distance "S" to the retracted position. The coil springs 38 cannot prevent this retraction because they have the smaller spring constant than the spring elements 34.

The position of the cam wheel 52, the slot 50 and the pin 48 are such that during the upward movement of the guide mechanism the smaller diameter portion of the cam wheel 52 engages the cam follower 58 so tha the specimen holder 2 is retracted by the distance "S" to the retracted position; during the downward movement of the guide mechanism 4 the larger diameter portion of the cam wheel 52 engages the cam follower 58 so that the specimen holder 2 is not retracted by the distance "S" and is in the unretracted position. The cam follower 28 changes between engaging the larger and smaller diameter portions of the cam wheel 52 when the guide member 4 is at the uppermost and lowermost positions.

The pin 48 is arranged so that its height relative to the microtome 60 is always the same as the height of the specimen holder 2. Thus, when the specimen holder 2 is at the lowermost position the pin 48 is also at the level of the lowermost position, and when the specimen holder 2 is at the uppermost position the pin 48 is also at the level of the uppermost position. This is important because it helps to prevent tilting of the drive during the cutting operation.

The direction of rotation of the drive wheel 42 can be reversed at any time. This causes the direction of movement of the guide mechanism 4, and hence the specimen holder 2 and the specimen clamping mechanism 86, to be reversed.

When the direction of rotation of the drive wheel 42 is reversed the pin 48 moves through the slot 50 through an arc of 180°, i.e. through one-half revolution of the drive wheel 42, until it engages the other end stop.

For example, if the drive wheel is first rotated in a clockwise direction then the pin 48 would engage the end stop 68 until the direction of rotation was changed to anticlockwise, when the pin 48 would move through the slot 50 until it engages the end stop 70. Continued anticlockwise rotation would cause the cam wheel 52 to begin rotating once more, but in an anticlockwise direction. The provision of the slot 50 prevents rotation of the cam wheel 52 in the anticlockwise direction from beginning immediately after rotation of the drive wheel 42 begins in the anticlockwise direction. If this movement of the cam wheel 52 was permitted to occur immediately after the beginning of rotation of the drive wheel 42, then the position of the cam wheel 52 would be placed out of synchronisation with the upward and downward movement of the guide mechanism 4 so that retraction occurred during the downward movement, and no retraction occurred during the upward movement.

The adjustments of the specimen holder 2 by the adjustment mechanism 6 are repeated according to the number of revolutions of the drive wheel 42. After each rotation the specimen holder 2 is further adjusted by a precise cutting-thickness adjustment distance towards the cutting knife 84. Simultaneously, during each half rotation of the drive wheel 42 to move the guide mechanism 4 from the lowermost position to the uppermost position, the specimen holder 2 is retracted by the distance "S" to the retracted position.

We claim:

1. A microtome having a knife for sectioning a specimen comprising, a stand, a vertically-slideable guide means mounted on said stand, drive means for inparting a reciprocating vertical motion to said guide means, a specimen holder slideably mounted on said guide means, said holder being slideable along a horizonal path extending toward the knife, adjustment means engaging said holder for moving the specimen holder along the horizonal path, retraction means connecting said adjustment means to said guide means and being operably connected to said drive means to move said specimen holder from an unretracted position to a retracted position, when actuated by said drive means.

2. A microtome according to claim 1 wherein a first biasing means urges the specimen holder toward the unretracted position.

3. A microtome according to claim 2 wherein said retraction means includes a lever, one end of said lever being pivotably mounted on said guide means and a horizonally-movable, vertically-orientated rail operably engaging the other end of said lever, said lever being connected to said adjustment means between said one end and said other end, and said rail being operably connected to said drive means, whereby movement of said rail is transferred to said specimen holder through said adjustment mechanism.

4. A microtome according to claim 3, wherein said biasing means comprises a spring disposed between said guide means and said specimen holder to urge the specimen holder.

5. A microtome according to claim 3 wherein said drive means includes a shaft, a wheel mounted on said shaft for rotation therewith, said retraction means includes a cam rotatably mounted on said shaft, coupling means connecting said wheel and said cam to provide associated motion, a follower means engaging said cam, and means linking said cam to said rail.

6. A microtome according to claim 5 wherein said coupling means provides action by the cam during upward movement of the guide means notwithstanding the direction the shaft is rotated.

7. A microtome according to claim 6 wherein said coupling means comprises a pin extending from said wheel parallel to said shaft to engage said cam, and said cam has an arcuate slot for receiving the distal end of said pin.

8. A microtome according to claim 7, wherein said cam wheel has a smaller radius over one-half of its periphery than over the other half of its periphery, the diametrically opposed transitions between different radii being continuous.

9. A microtome according to claim 3, wherein the other end of said lever carrys a bearing adapted to roll on said guide rail.

10. A microtome according to claim 7 wherein said follower means is slideably mounted on said stand and a bearing mounted on one end of follower means to engage said cam periphery.

* * * * *